United States Patent [19]
Hettche et al.

[11] Patent Number: 5,998,403
[45] Date of Patent: Dec. 7, 1999

[54] SALTS OF AZELASTINE HAVING IMPROVED SOLUBILITY USEFUL AT PROVIDING A CYTOPROTECTIVE EFFECT

[75] Inventors: Helmut Hettche, Dietzenbach; Reinhard Muckenschnabel, Frankfurt; Gerhard Scheffler, Bruchköbel; Ilona Fleischhauer, Offenbach; Wolfgang Mörick, Frankfurt, all of Germany

[73] Assignee: Asta Pharma Aktiengesellschaft, Frankfurt, Germany

[21] Appl. No.: 09/123,431

[22] Filed: Jul. 28, 1998

Related U.S. Application Data

[62] Division of application No. 08/691,415, Aug. 2, 1996, Pat. No. 5,859,003, which is a continuation of application No. 08/281,973, Jul. 29, 1994, abandoned, which is a continuation of application No. 07/519,172, May 4, 1990, abandoned.

[30] Foreign Application Priority Data

May 5, 1989 [DE] Germany .............................. 39 14 859

[51] Int. Cl.$^6$ ....................................................... A61K 31/55
[52] U.S. Cl. ................................................................. 514/212
[58] Field of Search ............................................... 514/212

[56] References Cited

U.S. PATENT DOCUMENTS 3,813,384  5/1974  VogelSang ........................... 260/239 A
4,868,175  9/1989  Engle .

FOREIGN PATENT DOCUMENTS 0 316 639  10/1988  European Pat. Off. .
63-218622  9/1988  Japan .
0 124 824  5/1990  Japan .

*Primary Examiner*—William R. A. Jarvis
*Attorney, Agent, or Firm*—Pillsbury Madison & Sutro LLP

[57] ABSTRACT

The present invention relates to salts of azelastine having improved solubility in water. The salts of the present invention are prepared by reacting azelastine with acetic acid, gluconic acid, lactic acid, or malic acid. The azelastine salts are effective in providing a cytoprotective effect.

2 Claims, 4 Drawing Sheets

SALTS OF AZELASTINE HAVING IMPROVED SOLUBILITY USEFUL AT PROVIDING A CYTOPROTECTIVE EFFECT

This is a division of application Ser. No. 08/691,415, filed Aug. 2, 1996, U.S. Pat. No. 5,859,003, which is a continuation of Ser. No. 08/281,973, filed Jul. 29, 1994, now abandoned, which is a continuation of Ser. No. 07/519,172, filed May 4, 1990, now abandoned.

The present invention relates to salts of azelastine which have improved solubility compared to previously known salts of azelastine.

BACKGROUND OF THE INVENTION

Azelastine is a phthalazinone derivative having the following structural formula:

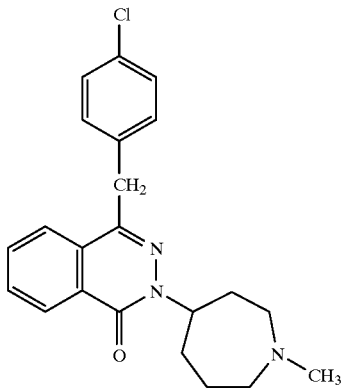

The chemical designation of azelastine is: 4-(4-chlorobenzyl)-2-(perhydro-1 methylazepine-4-yl)-1-(2H) phthalazinone. Azelastine is particularly useful in asthma prophylaxis. Azelastine also has anti-allergic and antihistaminic properties, see German Patent No. 21 64 058.

Azelastine dissolves to the extent of 0.005% in water at 20° C.

Previously used salts of azelastine display the following solubility in water at 20° C.:

| | |
|---|---|
| hydrochloride | 1% |
| embonate | 0.0015% |

Other salts of azelastine have the following solubilities:

| | |
|---|---|
| succinate | |
| phospate | solubility |
| maleate | in water at 20° C. |
| citrate | ca. 1% |
| methane sulphonate | |
| fumarate | |
| toluene sulphonate | under 1% |
| benzene sulphonate | |
| tartrate | |

The solubilities quoted, as well as the marked dependence of solubility on temperature, result in the salts not being suitable for the preparation of pharmaceutical formulations having a higher content of dissolved azelastine. The preparation of locally applied formulations, in particular those with a limited water content (for example emulsion ointments and creams as well as gels) call for the availability of more highly concentrated aqueous solutions in order to provide the required amounts of active substances to the skin or mucous membrane.

SUMMARY OF THE INVENTION

Therefore, it is an object of the present invention to provide salts of azelastine having higher solubility in water and to further increase the solubility of these salts. On the other hand, the invention seeks to increase the tolerance of the formulations prepared therefrom, for example on the skin or mucous membrane.

In accordance with the invention, it was surprisingly found that it is possible to prepare stable pharmaceutical formulations, in particular solutions, having a high active substance content (for example up to 20–50%) from salts of azelastine with acetic acid, gluconic acid, lactic acid or malic acid (azelastine acetate, azelastine gluconate, azelastine lactate or azelastine malate).

The azelastine used to prepare these salts is described in German Patent No. 21 64 058.

The salts of the present invention are prepared by reacting 4-(4-chlorobenzyl)-2(perhydro-1-methyl-azepine-4-yl)-1-(2H) phthalazinone with acetic acid, gluconic acid or gluconic acid-delta-lactone, lactic acid or malic acid. This reaction can take place with or without solvent at temperatures between 20° C. and 140° C., preferably 50° C. and 120° C. The components are preferably reacted in each case in molar ratio (1 mol azelastine with 1 mol acid). A slight excess (for example up to 0.1 mol) of acid is possible. Should the salts not be isolated, that is, should these be used in the form of solutions or suspensions, the acid may be used in greater excess, up to a maximum of 1 mol excess (i.e. 2 mol acid per 1 mol azelastine), preferably up to 0.5 mol excess.

Solvents that may, for example, be used for this reaction are lower alcohols (for example alcohols containing 1–6 carbon atoms such as methanol, ethanol, n-propanol, isopropanol, n-butanol, 1,2-dihydroxypropane, 1,4-butandiol, n-pentanol, 3-pentanol, n-hexanol), lower ketones (for example with 1–6 carbon atoms such as acetone, 2-butanone, methylisobutylketone), polyalkylene glycols (wherein "alkylene" represents an alkylene group containing 2, 3 or 4 carbon atoms) with molecular weights between 190 and 7500 and cyclic saturated alcohols with 4 to 8, preferably 4 to 6 carbon atoms, such as for example glycofurol, as well as pharmaceutically acceptable organic acids and mixtures of these agents, in water.

Should gluconic acid-delta-lactone be used instead of gluconic acid, a certain amount of water must be present (for example 1 mol water per 1 mol lactone). It is for example advantageous to use gluconic acid-delta-lactone since it is commercially available in crystalline form and is rapidly hydrolyzed in water to gluconic acid. Preparation may, for example, be in the following manner:

Azelastine is optionally suspended in a solvent (e.g., ethanol or 1,2-dihydroxypropane) and treated with a solution prepared at a temperature between 20° C. and 140° C. composed of 1 mol gluconic acid-delta-lactone in an aqueous solvent (e.g., ethanol or 1,2-dihydroxypropane) or with 1 mol of the above-mentioned acids, with or without solvent. The reaction mixture is allowed to continue to react for some time, preferably with heating to 50 to 70° C., and then any optionally present solvents are removed by evaporation. The remaining residue is post-evaporated with alcohol and dried in a vacuum at elevated temperature.

The salt is obtained in a yield of 90%.

The salts of the invention in solid form have the following melting points:

| acetate: | 116–118° C. | gluconate: | 61–66° C. |
|---|---|---|---|
| lactate: | 139–140° C. | malate: | 154–155° C. |

Acetate, lactate and malate salts of azelastine are obtained in the form of a white crystalline powder. The gluconate is obtained as a yellowish crystalline powder The solubility of the salts of azelastine of the invention in water at room temperature is for example:

acetate: more than 10%
gluconate: up to 5–55%
lactate: more than 10%
malate: 3%

Solutions of azelastine acetate, azelastine guconate, azelastine lactate or azelastine malate may also be obtained by mixing azelastine in the form of the base with the corresponding acid in water or aqueous solvents (polyethylene glycol-water, propylene glycol-water) (for example by stirring or suspension at a temperature between 20° C. and 80° C.).

Should gluconic acid-delta-lactone be used in place of gluconic acid, the presence of water is required, this amounting to at least 1 mole water for each 1 mole of gluconic acid-delta-lactone.

Addition of excess amounts of acid increases the solubility of the salts. For example a 1-fold, preferably a 0.5-fold, in particular a 0.25-fold excess of acid may be used. Solubility may also be further enhanced by addition of an alkali salt (Na, K) or ammonium salt of the appropriate acid (for example up to 1 mol alkali or ammonium salt, in particular up to 0.5 mol salt per 1 mol azelastine salt).

The pH value of the solutions or formulations using the salts of the invention is, in the acid range, generally not under 3, preferably not under 3.5, in particular not under 4; in the upper range it is generally not over 8, preferably not over 7.5.

For example, the addition of acids yields the following solubility and following pH value of the aqueous solution:

| Salt | Excess acid (mol) | Solubility | pH value |
|---|---|---|---|
| Acetate | 0 | 2% | 6.35 |
|  | 0.1 | 3% | 5.52 |
|  | 0.25 | 10% | 5.1 |
| Gluconate | 0.5 | 10% | 4.5 |
| Lactate | 0 | 3% | 5.15 |
|  | 0.1 | 5% | 4.6 |
|  | 0.25 | 10% | 4.1 |
| Malate | 0 | 5% | 3.85 |

The solutions also remain clear when stored for 7 days at 25° C. and in daylight as well as for 7 days left standing in a refrigerator at 7° C. without crystal formation or clouding. The solutions prepared according to the invention therefore present advantages in stability and in improved storage.

Solutions of this type are aqueous solutions which can, for example, also contain conventional stabilizers, buffer substances and other conventional physiologically acceptable auxiliary substances. These are either purely aqueous solutions or aqueous solutions in which part of the water has been replaced by one or several other physiologically acceptable liquid agents (up to 20 percent by weight). Liquid agents of this type may, for example, be: $C_2$–$C_4$-alkanols, liquid polyethylene glycols (for example up to molecular weight 1500).

The pharmaceutical dosage forms are prepared from the azelastine salts or their solutions using conventional standard processes.

These can be used to prepare solutions, tinctures, lotions, emulsions, gels, creams, ointments, shampoos and plasters.

The concentrations of azelastine (related to the base) can for example lie between 0.1–50% by weight, preferably between 0.1–20% by weight, more preferably between 1–10% by weight, and in particular 2–5% by weight or 3–5% by weight.

High concentrations in solutions (in particular aqueous solutions) between 20 and 50 percent by weight may be considered in particular for azelastine gluconate. The gluconate may of course also be used in concentrations lower than 20 percent by weight. Concentrations in solutions up to 20 percent by weight may in particular be considered for the acetate and lactate. Concentrations in solutions up to 5% may in particular be considered for the malate.

The following concentrations may, for example, be considered for the individual salts in the solutions (preferably aqueous solutions):

azelastine gluconate: 0.1–50, preferably 1–50 percent by weight
azelastine acetate: 0.1–20, preferably 1–20 percent by weight
azelastine lactate: 0.1–20, preferably 1–20 percent by weight
azelastine acetate: 0.1–5, preferably 1–3 percent by weight The advantage of these medicinal forms is, on the one hand, improved stability. Thus there are none of the crystal separations and emulsion separations seen with medicinal forms produced from hitherto known salts. The other advantage is their improved efficacy which is governed by the higher concentration and enhanced permeation of the azelastine through the skin and mucus membrane.

The pharmaceutical formulations and compositions contain azelastine or its physiologically acceptable salts as active substance. The active substance is optionally present in a mixture with other pharmacologically or pharmaceutically active substances. The preparation of the pharmaceutical composition is accomplished in known manner, it being possible to use known and conventional pharmaceutical auxiliary substances as well as other conventional carriers and diluents.

Carriers and auxiliary substances of this type that may be used are substances which are listed in the following literature references that are quoted or recommended as auxiliary substances for pharmacy, cosmetics and related fields: Ullmanns Encyclopädie der technischen Chemie, Volume 4 (1953), page 1 to 39; Journal of Pharmaceutical Sciences, Volume 52 (1963), page 918 et seq., H. v. Czetsch-Lindenwald, Hilfsstoffe für Pharmazie und angrenzende Gebiete; Pharm. Ind., Issue 2, 1961, page 72 et seq.; Dr. H. P. Fiedler, Lexikon der Hilfsstoffe für Pharmazie, Kosmetik und angrenzende Gebiete Cantor KG, Aulendorf in Württemberg 1981.

Examples thereof are gelatins, natural sugars such as cane sugar or lactose, lecithin, pectin, starch (for example corn starch), cyclodextrins and cyclodextrin derivatives, polyvinyl pyrrolidone, polyvinyl acetate, gum arabic, alginic acid, tylose, talcum, lycopodium, silica gel (for example colloidal), cellulose, cellulose derivatives (for example cellulose ethers in which the cellulose hydroxy groups are partially etherified with lower saturated aliphatic alcohols and/or lower saturated aliphatic oxyalcohols, for example methoxypropyl cellulose, methyl cellulose, hydroxypropylmethyl cellulose, hydroxypropylmethyl cellulose phthalate); fatty acids as well as magnesium, calcium or aluminum salts of fatty acids with 12 to 22 carbon atoms, in particular saturated (for example stearates), emulsifiers, oils and fats, in particular vegetable (for example peanut oil, castor oil, olive oil, sesame oil, cottonseed oil, corn oil, wheat germ oil, sunflower seed oil, cod liver oil, in each case also hydrated; mono-, di- and triglycerides of saturated fatty acids $C_{12}H_{24}O_2$ to $C_{18}H_{36}O_2$ and their mixtures), pharmaceutically acceptable mono- or multivalent alcohols and polyglycols such as polyethylene glycol as well as derivatives thereof, esters of aliphatic saturated or unsaturated fatty acids (2 to 22 carbon atoms, in particular 10–18 carbon atoms) with monovalent aliphatic alcohols (1 to 20 carbon atoms) or multivalent alcohols such as glycols, glycerin, diethylene glycol, pentaerythritol, sorbitol, mannitol and the like, which may optionally also be etherified, esters of citric acid with primary alcohols, acetic acid, benzyl benzoate, dioxolanes, glycerin formals, tetrahydrofurfuryl alcohol, polyglycol ether with $C_1$–$C_{12}$ alcohols, dimethyl acetamide, lactamides, lactates, ethyl carbonates, silicones (in particular medium viscous polydimethyl siloxanes).

For the preparation of solutions it is, for example, possible to use water or physiologically acceptable organic solvents, such as ethanol, 1,2-propylene glycol, polyglycols and their derivatives, dimethyl sulfoxide, fatty alcohols triglycerides, partial esters of glycerin, paraffins and the like.

For injectable solutions or suspensions it is, for example, possible to use non-toxic parenterally acceptable diluents or solvents such as for example: water, 1,3-butane diol, ethanol, 1,2-propylene glycol, polyglycols in mixture with water, Ringer's solution, isotonic sodium chloride solution or also solidified oils including synthetic mono or diglycerides or fatty acids such as oleic acid.

It is possible to use known and conventional diluting agents or emulsifiers in the preparation of the formulations. Diluting agents and emulsifiers which may for example be used are: polyvinyl pyrrolidone, sorbitan fatty acid esters such as sorbitan trioleate, phosphatides such as lecithin, acacia, tragacanth, polyoxyethylated sorbitan mono-oleate and other ethoxylated fatty acid esters of sorbitan, polyoxyethylated fats, polyoxyethylated oleotriglycerides, linolized oleotriglycerides, polyethylene oxide condensation products of fatty alcohols, alkylphenols or fatty acids or also 1-methyl-3-(2-hydroxyethyl)-imidazolidone-(2). Polyoxyethylated means here that the appropriate substances contain polyoxyethylene chains the degree of polymerization of which is generally between 2 and 40, and in particular between 10 to 20.

Polyoxyethylated substances of this type may for example be obtained through reaction of hydroxyl group containing compounds (for example mono or diglycerides or unsaturated compounds such as those containing oleic acid radicals) with ethylene oxide (for example 40 mol ethylene oxide per mol glyceride).

Examples of oleotriglycerides are olive oil, peanut oil, castor oil, sesame oil, cottonseed oil, corn oil. See also Dr. H. P. Fiedler "Lexikon der Hilfsstoffe für Pharmazie, Kosmetik und angrenzende Gebiete" 1971, p. 191–195.

Moreover the addition of preservatives, stabilizers, buffer substances, for example calcium hydrogen phosphate, colloidal aluminum hydroxide, colorants, antioxidants and complex formers (for example ethylene diaminotetraacetic acid) and the like is also possible.

Adjustment to a pH range of ca. 3 to 7 using physiologically acceptable acids or buffers is optionally possible to stabilize the active substance molecule. A pH value which is as neutral as possible or weakly acidic (up to pH 3.5) is generally preferred.

For the preparation of formulations for application to the skin, it is possible to use the above mentioned substances and spreadable or liquid hydrocarbons such as Vaseline or paraffin or gels made of alkanes and polyethylene, fats and oils of vegetable or animal origin which may in part also be hydrated or synthetic fats such as glycerides of the fatty acids $C_8$–$C_{18}$ as well as beeswax, cetyl palmitate, wool wax, wool wax alcohols; fatty alcohols such as cetyl alcohol, stearyl alcohol, polyethylene glycols of molecular weight 200 to 20,000; liquid waxes such as isopropyl myristate, isopropyl stearate, ethyl oleate; emulsifiers such as sodium-, potassium-, ammonium salts of stearic acid or palmitic acid as well as triethanolamine stearate, alkali salts of oleic acid, castor oil acid, salts of sulfurated fatty alcohols such as sodium lauryl sulphate, sodium cetyl sulphate, sodium stearyl sulphate, salts of gallic acid, sterols such as cholesterol, partial fatty acid esters of multivalent alcohols such as ethylene glycol monostearate, glycerol monostearate, pentaerythritol monostearate, partial fatty acid esters of sorbitan, fatty acid esters of polyoxyethylene, partial fatty acid esters of polyoxyethylene sorbitan, sorbitol ethers of polyoxyethylene, fatty alcohol ethers of polyoxyethylene, fatty acid esters of saccharose, fatty acid esters of polyglycerol, lecithin.

Antioxidants that may for example be used are sodium metabisulphite, ascorbic acid, gallic acid, gallic acid alkyl ester, butylhydroxyanisole, nordihydroguaiacic acid, tocopherols as well as tocopherols+synergists (substances which bind heavy metals through complex formation, for example lecithin, ascorbic acid, phosphoric acid). The addition of the synergists substantially enhances the antioxygenic effect of the tocopherols.

Preservatives that may, for example, be used are sorbic acid, p-hydroxybenzoic acid esters (for example lower alkyl esters), benzoic acid, sodium benzoate, trichloro-isobutyl alcohol, phenol, creosol, benzethonium chloride and formalin derivatives.

The pharmaceutical and galenic handling of the active substances is carried out according to conventional standard methods. For example, active substance(s) and auxiliary agents or carriers are well mixed by stirrin% or homogenizing (for example using conventional mixers), the operation generally being carried out at temperatures between 20 and 80° C., preferably 20 to 50° C., in particular at room temperature. Reference is also made to the following standard reference book: Sucker, Fuchs, Speiser, Pharmazeutische Technologie, Thieme-Verlag Stuttgart, 1978.

The application may be on the skin or mucous membrane or to the inside of the body, for example oral, enteral, pulmonal, rectal, nasal, vaginal, lingual, intravenous, intraarterial, intracardial, intramuscular, intraperitoneal, intracutaneous, subcutaneous.

The parenteral formulation forms are in particular sterile or sterilized preparations.

Should the acids used contain optically active carbon atoms, the salts of the invention may be present in the form of the racemates, the possible diastereomeric forms and in the form of the optically active dextro- and laevo-rotatory forms. Preparation is effected using the corresponding racemates or optically active forms of the starting acids or by means of subsequent racemate splitting or separation of the salts of the invention using conventional methods therefor.

BRIEF DESCRIPTION OF THE DRAWINGS

The infra-red spectra of the acetate, malate, lactate and gluconate salts of azelastine are shown in FIG. 1, FIG. 2, FIG. 3 and FIG. 4 respectively.

The pharmacological effect of the azelastine salts of the invention corresponds to that of azelastine (for example that of azelastine hydrochloride). They are thus also effective as anti-allergy agents (histaminolytically) and in asthma prophylaxis. In addition, in common with azelastine, they have anti-inflammatory and cytoprotective effects and are effective against psoriasis disorders.

Figure 1:
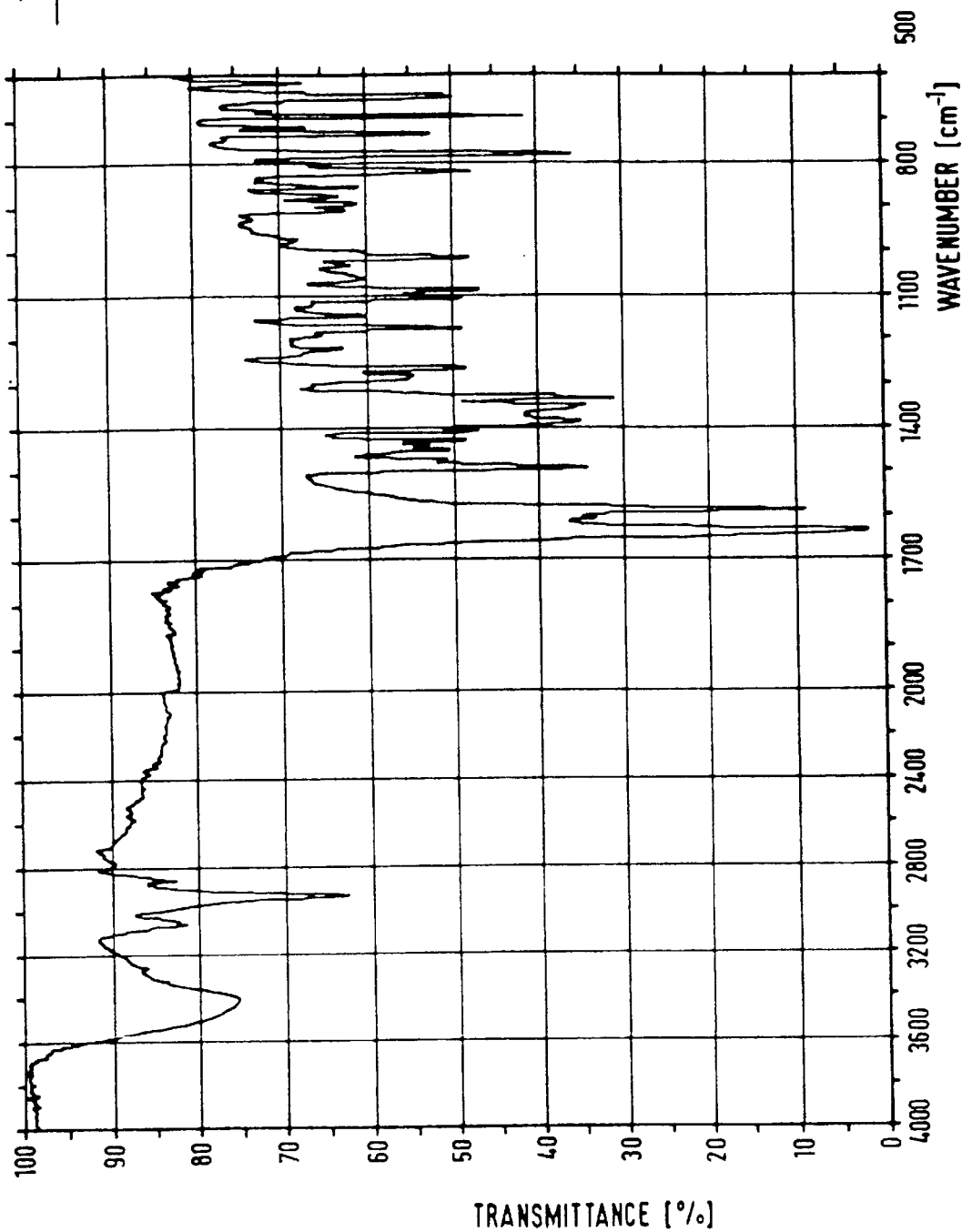
Figure 2:
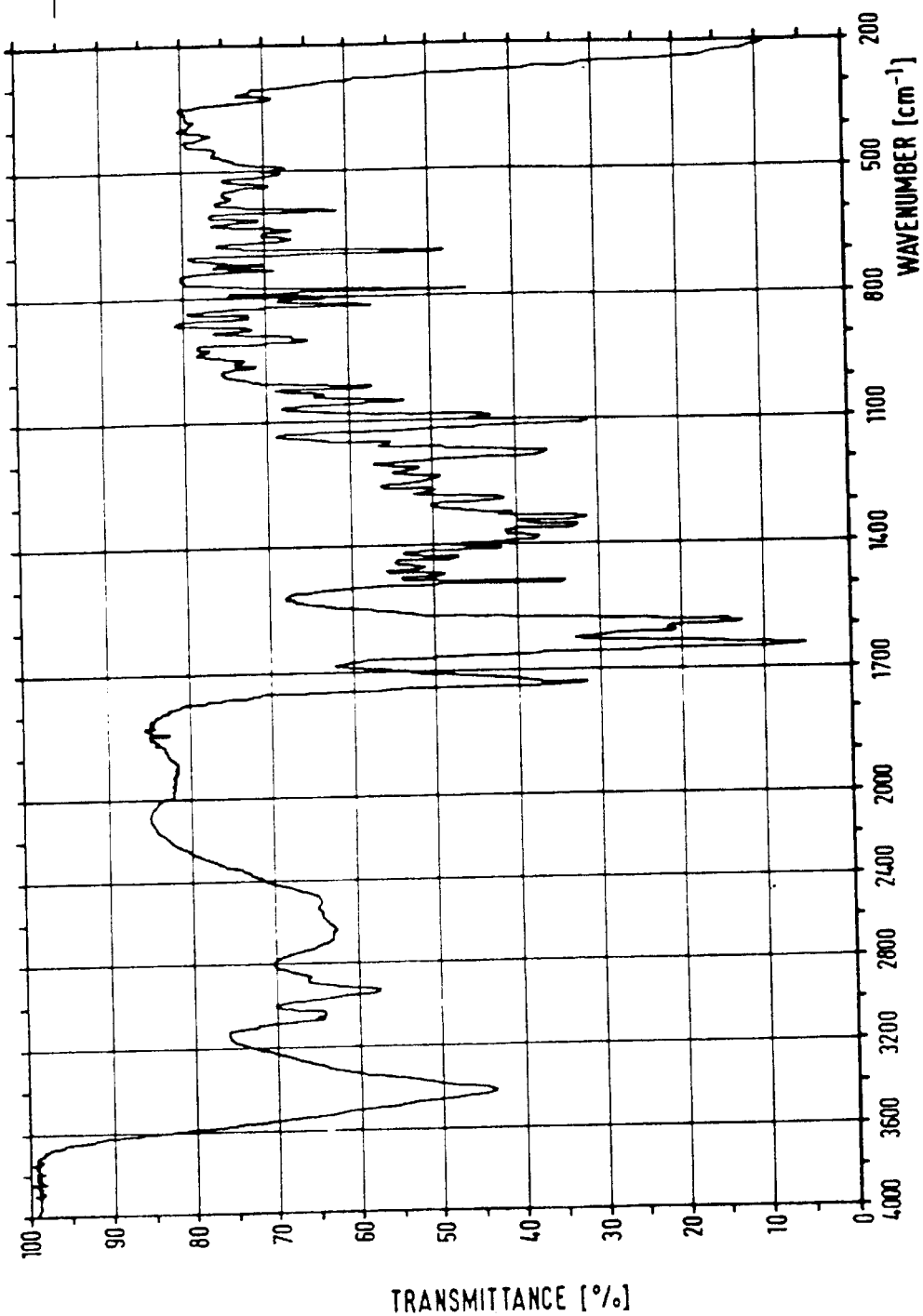
Figure 3:
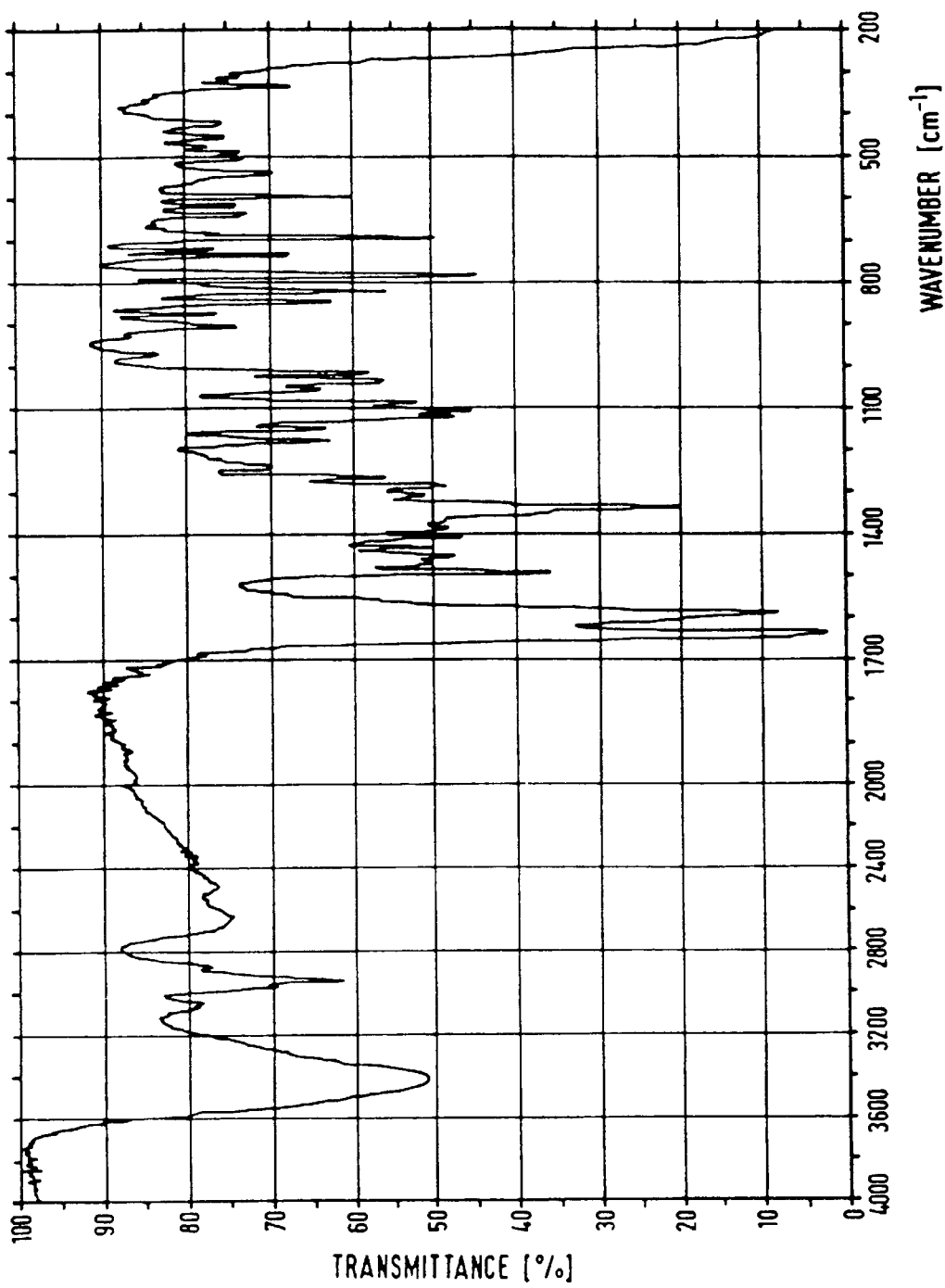
Figure 4:
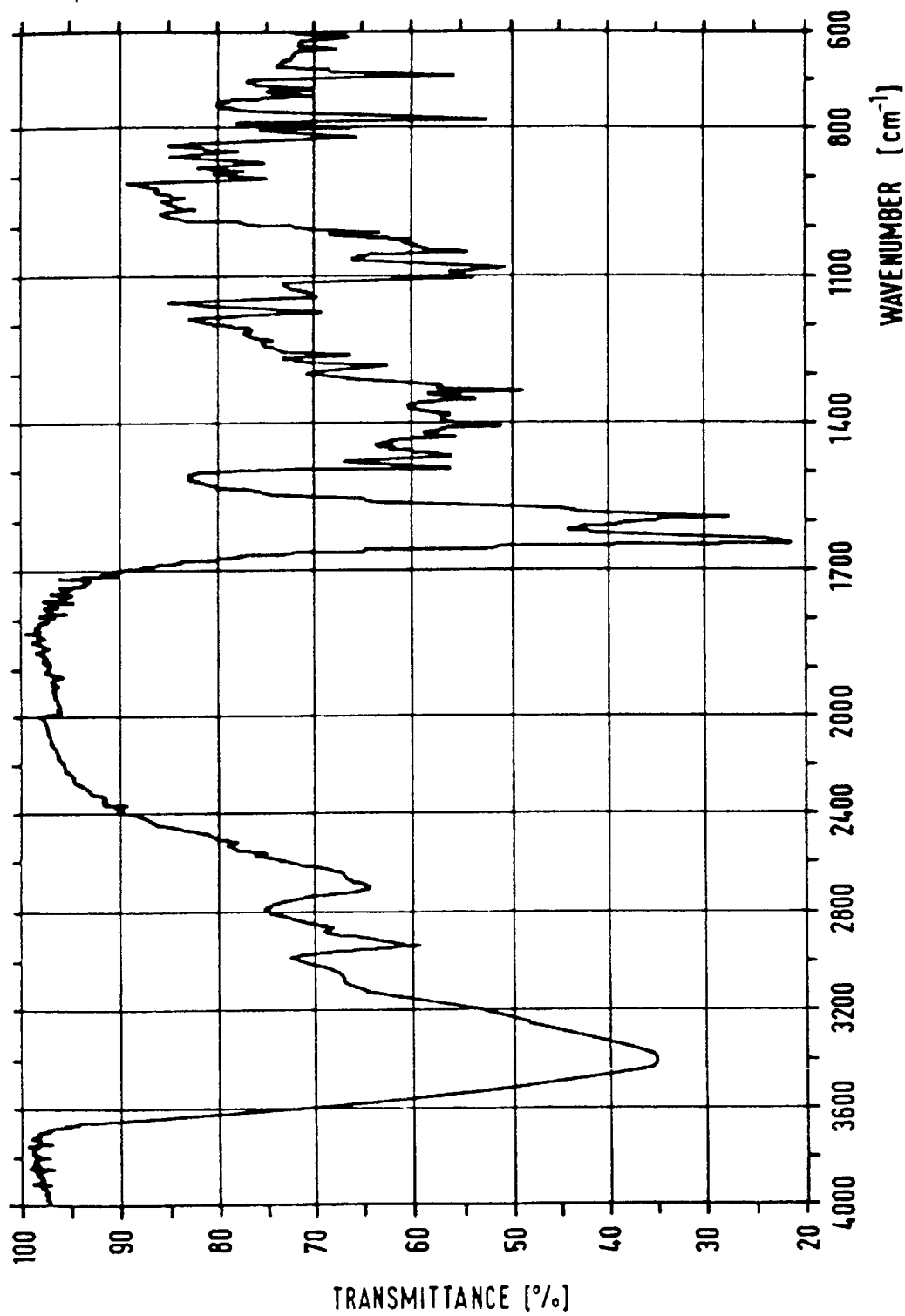

Inflammatory disorders that apply in particular are also colitis ulcerosa and related disorders (for example Crohn's disease, inflammatory bowel disease), gastritis, rheumatoid arthritis, inflammatory and degenerative forms of rheumatism).

Psoriasis disorders are understood to include: skin disorders associated with hyperkeratoses, in particular psoriasis.

With regard to the histaminolytic or anti-allergic effect: the salts of the invention are characterized by exceptionally high activity in parenteral and, above all, oral application as well as by a long duration of action (for example in the histamine aerosol trial in guinea pigs or in the histamine or histamine-liberator weal test in Man).

The histaminolytic (anti-allergic) effect was tested in the histamine-aerosol test in guinea pigs. The animals inhaled an aerosol of an aqueous solution of histamine dihydrochloride (concentration 4 mg/ml). In untreated animals the inhalation led, within 2 minutes, to the most severe dyspnoea (suffocating cramps, lateral position). The asthma prophylactic effect can for example be determined in the "Ovalbumin asthma" screening model in waked guinea pigs 2 hours prior to allergy exposure in peroral administration. The $ED_{50}$ in this trial for the salts of the invention is on average in the region of 0.3 mg/kg.

In order to establish the histaminolytic effect, the substances were applied subcutaneously or orally to groups of 8–10 animals. The animals were then exposed at different times to the effects of the histamine aerosol. They were considered to be protected if they tolerated the inhalation of the aerosol for 10 minutes without severe dyspnoea (lateral position).

For evaluation purposes the mean effective doses ($ED_{50}$ {mg/kg}) were determined using probit analysis from the relationship between the dosage logarithms and the incidence of protection.

The effect may be seen from the following tables:
Histaminolytic effect in the histamine aerosol trial in guinea pigs, subcutaneous application 1 hour (1 h) before the aerosol

|  | $ED_{50}$ (mg/kg) |
| --- | --- |
| compounds of the invention | 0.031 |

Histaminolytic effect in the histamine aerosol trial in guinea pigs, application per os 2 hours (2 h) and 8 hours (8 h) before the aerosol

|  | $ED_{50}$ | |
| --- | --- | --- |
|  | 2 h-value | 8 h-value |
| compounds of the invention | 0.037 | 0.029 |

With regard to the anti-inflammatory and cytoprotective effect:

For example in the case of arachidonic acid-induced mouse ear edema, a dose of 3 mg peroral/kg body weight mouse achieved a 20–30% inhibition of the edema and topical application of a dose of 0.25 mg/mouse ear achieved a 30–40% inhibition. In rat paw edema (induced by carragheen, determination of paw volumes after one hour) a peroral dose of for example 3.5–4.5 mg/kg rat achieved a 50% inhibition of edema formation. The minimum effective dose in the above cited animal experiments is, for example, 1–2 mg/kg orally or 10 mg/kg in topical application (10 mg/kg correspond approximately to 0.25 mg/cm$^2$ body surface).

The compounds of the invention also inhibit ulcerous intestinal inflammation in the rat triggered by indomethacin (P. Del Soldato et al., Agents and Actions, Volume 16, 5, Birkhäuser Verlag, Basel 1985, pages 393–396) in a dosage range of for example 8–80 mg/kg in a dose-dependent manner. This model shows the effect in colitis ulcerosa in particular. For example in the above mentioned experimental method with peroral administration 5 times of, in each case, 50 mg/kg body weight of rat (application schedule according to Del Soldato) an approximately 50% inhibition of the inflammation is achieved.

With regard to the effect against psoriasis and testing of this effect:

Mice (average weight 25 g) received 1 mg/kg daily of the salt of the invention orally for 7 days. On Day 8 the top layer of skin was removed using sandpaper.

This mechanical irritation and removal of the top layer of skin causes an acute reaction with morphological similarities to the psoriasis reaction. In addition, there is an increase in the leucotrien content of the dermis and epidermis. This correlates with a reduction in prostaglandin concentration. These changes, too, are typical for psoriasis. These changes were not encountered after prior treatment with the salts of the invention. They normalized or even lowered the dermal or epidermal leucotrien concentration and increased the concentration of prostaglandins.

DETAILED DESCRIPTION OF PREFERRED EMBODIMENTS

The invention is illustrated by the following examples.

EXAMPLE 1

Solution Containing 3.47% Azelastine Acetate (Corresponding to 3% Azelastine)

86.24 ml 1N acetic acid are mixed with stirring with 850 ml purified water. 30 g azelastine are added to this mixture and stirring is continued until a clear solution is obtained. The solution is then diluted to 1000 ml with purified water.

The pH value of the solution so obtained is 5.5, the molar ratio azelastine:acetic acid is 1:1.1.

EXAMPLE 2

Cream Containing 5.785% Azelastine Acetate (Corresponding to 5% Azelastine)

50 g polyoxyethylene-40-stearate (trade name: Myrj$^R$ 52), 80 g cetyl stearyl alcohol, 200 g white Vaseline, 150 g viscous paraffin and 5 g polydimethylsiloxane (Dimethicone) are melted together in a homogenizing apparatus at 80° C. 1.26 g methyl-4-hydroxybenzoate and 0.533 g propyl-4-hydroxybenzoate are dissolved in the melt.

298.207 g purified water are heated to 70° C. and 1.4 g methyl-4-hydroxybenzoate and 0.6 g propyl-4-hydroxybenzoate is dissolved therein. 163 g 1N-acetic acid are added to this solution. 50 g azelastine are added with stirring to the so-obtained solution. The ca. 70° C. warm solution is added slowly and with stirring to the above-obtained fat melt, tempered to about 80° C. The emulsion obtained is homogenized and cooled to room temperature with stirring.

The pH value of the emulsion is 5.2, the molar ratio of azelastine:acetic acid is 1:1.25.

EXAMPLE 3
Cream with 3.71% Azelastine Lactate (Corresponding to 3% Azelastine)

470.877 g purified water are heated to about 70° C. and 1.4 g methyl-4-hydroxybenzoate and 0.6 g propyl-4-hydroxybenzoate dissolved therein. 10.33 g 90% lactic acid are added to this solution and 30 g azelastine added to the solution with stirring.

The ca. 70° C. warm solution is added slowly and with stirring to the fat melt of Example 2 tempered to about 80° C. The emulsion obtained is homogenized and cooled with stirring to room temperature.

The pH value of the emulsion is 4.5, the molar ratio azelastine:lactic acid is 1:1.1.

EXAMPLE 4
Gel Containing 15.13% Azelastine Gluconate (Corresponding to 10% Azelastine)

796.3 g purified water are heated to about 70° C. and 1 g methyl-4-hydroxybenzoate and 0.4 g propyl-4-hydroxybenzoate dissolved therein. 58.3 g gluconic acid-delta-lactone are then dissolved in the solution. The solution is maintained at a temperature of 70° C. for 1 hour, during which the gluconic acid-delta-lactone hydrolyses to gluconic acid. 100 g azelastine are then dissolved in the solution with stirring.

20 g polyoxyethylene (20 mol ethylene oxide)-sorbitanlaurate (Polysorbat 20) and 24 g hydroxyethyl cellulose (degree of molar substitution: 2.5, viscosity of the 2% solution: 100 000 mPa·sec) are then added one after another to the solution cooled to room temperature.

Stirring is then continued until a clear gel is obtained.

pH-value of the gel: 4.0
The molar ratio azelastine:gluconic acid is 1:1.25.

EXAMPLE 5
Fatty Ointment with 4.05% Azelastine Malate (Corresponding to 3% Azelastine)

779.5 g white Vaseline and 30 g polyoxyethylene-20-stearyl ether (trade name Brij$^R$78) are melted together at a temperature of about 75° C. 40.5 g azelastine malate are suspended in 150 g viscous paraffin. This suspension is added with stirring to the above melt. The ointment is then cooled to room temperature with stirring.

What is claimed is:

1. A method of providing a cytoprotective effect in a subject in need thereof, said method comprising administering to said subject an effective dose of a pharmaceutical composition in the form of an aqueous solution, comprising:

a salt of azelastine selected from a member of the group consisting of azelastine acetate, azelastine gluconate, azelastine lactate and azelastine malate wherein when the salt is azelastine acetate the solubility of the salt in aqueous solution is at least about 2%, when the salt is azelastine malate or azelastine lactate the solubility of the salt in aqueous solution is at least about 3%, and when the salt is azelastine gluconate the solubility of the salt in aqueous solution is at least about 5%, and a member of the group consisting of pharmaceutically-acceptable carriers and diluents therefor.

2. The method as set forth in claim 1 wherein the salt is azelastine acetate or azelastine lactate and the solubility of the salt in aqueous solution is at least about 10%.

* * * * *